United States Patent [19]

Leonard

[11] 4,240,473

[45] Dec. 23, 1980

[54] INSERT FOR INJECTING A LIQUID PRODUCT INTO A BORE

[75] Inventor: Henri Leonard, Besancon, France

[73] Assignee: Micro-Mega S.A., Besancon, France

[21] Appl. No.: 3,975

[22] Filed: Jan. 16, 1979

[30] Foreign Application Priority Data

Feb. 10, 1978 [FR] France ................................. 78 04802

[51] Int. Cl.³ .......................... B65B 3/04; F16L 21/02
[52] U.S. Cl. ....................................... 141/91; 141/312; 285/338; 433/114
[58] Field of Search .................... 141/349, 312, 85, 89, 141/91, 311 R, 312, 383, 392; 285/107, 109, 338; 433/114

[56] References Cited

U.S. PATENT DOCUMENTS

| | | | |
|---|---|---|---|
| 3,352,333 | 11/1967 | Glasgow et al. ...................... | 141/312 |
| 4,047,497 | 9/1977 | Grobler ................................ | 141/312 |

*Primary Examiner*—Frederick R. Schmidt

*Attorney, Agent, or Firm*—Robert E. Burns; Emmanuel J. Lobato; Bruce L. Adams

[57] ABSTRACT

This composite insert for injecting a liquid product under pressure into a member provided with an internal bore comprises first and second coaxial rigid sockets surrounding the outlet aperture of the container filled with said product, the first socket comprising an external flange and the second socket comprising an internal shoulder adapted to engage an internal abutment element of the member, the front end of the second socket comprising an external flange. A flexible resilient sleeve fits around the second socket and bears with its ends against the external flanges of the first and second sockets so that when an axial pressure is exerted against the second socket by means of the internal abutment element of the member the second socket is sunk more or less into the first socket, thus causing an elastic deformation of the sleeve which develops a bead engaging in a fluid-tight manner the wall of the inner bore of the member. This insert is suitable notably for lubricating and cleaning dental handtool holders.

4 Claims, 2 Drawing Figures

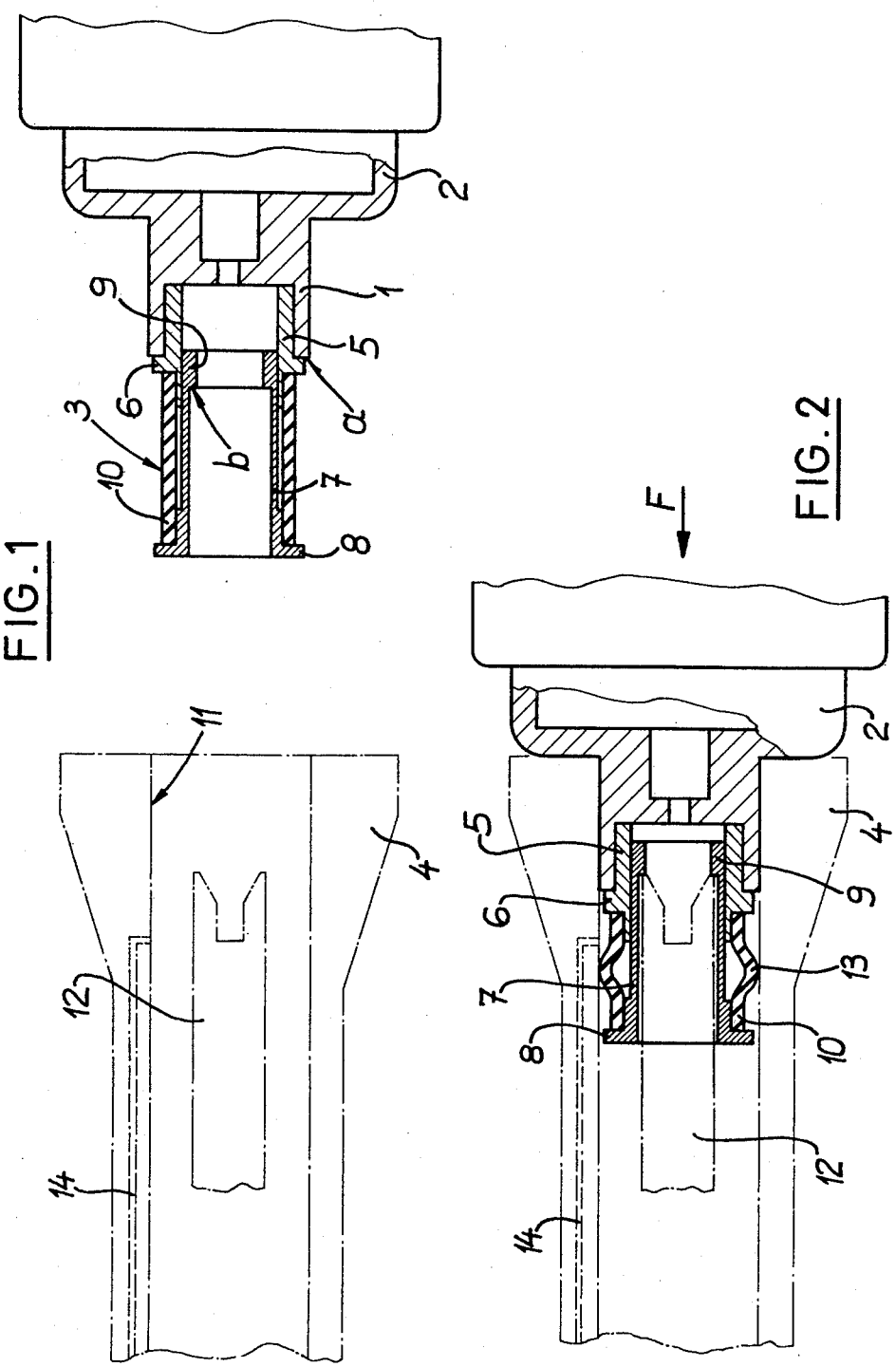

INSERT FOR INJECTING A LIQUID PRODUCT INTO A BORE

FIELD OF THE INVENTION

The present invention relates to an insert for injecting a liquid product from a pressurized container into a member provided with an internal bore.

This invention is directed more particularly to the injection of a lubricating or cleaning product into a dentist's handtool that can be driven by motor. However, it should not be regarded as being strictly limited to this specific application.

DESCRIPTION OF THE PRIOR ART

Modern dental handtools revolve at relatively high speeds of the order to 400 to 120,000 r.p.m., according to their type and specific purposes; they are high-precision tools requiring a regular maintenance in order properly to clean and lubricate their rotary component elements.

It is known to service these handtools by means of cleaning and/or lubricating products mostly of the aerosol type contained in vessels also filled with a suitable propergol. The end portion of the handtool of which the inner cavity has to be cleaned or lubricated is pressed against the valve normally provided on the pressurized container, this manual pressure causing the valve to open and the aerosol to be released by the propergol pressure into the aforesaid cavity.

During this lubrication or cleaning operation it is a very frequent occurrence that the product flows to the rear of the handtool and eventually smears the outer surface thereof, which is rather objectionable and compels the surgeon-dentist to wipe the handtool before re-using it. Moreover, certain dental handtools are provided with inner conduits and passages, notably for the circulation of a cooling fluid such as air or water, and these conduits and passages should normally be kept free of any lubricant.

SUMMARY OF THE INVENTION

It is the essential object of the present invention to provide a composite insert adapted to fit both on the handtool and on the valve end of the pressurized container so that the cleaning or lubricating product can be injected into the handtool without any risk of causing this product to flow back to the rear portion of the handtool or to choke the independent passages, ports or conduits to which no lubricant should be delivered. This type of insert is also applicable whenever a liquid product has to be injected into a member without allowing the product to overflow to the outside.

For this purpose, the composite or three-element insert according to the present invention is characterized in that it comprises a first, relatively rigid socket provided with an external flange and adapted to be fitted into the bore of a cylindrical collar surrounding the outlet or valved orifice of the container filled with the product in the form of an aerosol associated with a suitable propergol; a second, likewise rigid socket having its rear portion fitted telescopically in the first socket and provided with an annular bearing surface consisting more particularly of a shoulder formed on its cylindrical inner surface and adapted to bear against an inner, abutment-forming member of the handtool or other device into which the product has to be injected, the front end of this second socket being formed with an external flange; and, finally, a third element in the form of a flexible and resilient sleeve of cylindrical configuration surrounding the front portion of the second external socket, the ends of this sleeve engaging the registering annular surfaces of first and second external sockets, whereby when an axial force is exerted against the second socket the latter is caused to penetrate somewhat into the first socket so as to exert an axial compressive force against the flexible resilient sleeve and cause the elastic deformation thereof in the form of a beadlike swollen portion engaging the inner surface of bore of the handtool or other device to be lubricated and/or cleaned, this swollen portion positively sealing the passage from the outlet of the container to the registering end of the aforesaid bore.

This composite insert is applicable to various types of members having inlet apertures of different diameters, the magnitude of the bead formed by the swollen portion of the flexible resilient sleeve depending on the inner diameter of the inlet opening of the tool holder.

In order to afford a clearer understanding of this invention and of the manner in which the same may be carried out in actual practice, reference will now be made to the attached drawing illustrating diagrammatically by way of example a typical form of embodiment of the invention as applied to a container filled with an aerosol for lubricating dental handtools.

BRIEF DESCRIPTION OF THE DRAWING

FIG. 1 is a part-sectional, part-elevational view of the composite insert of this invention fitted to the outlet or valve end of a pressurized container filled with a product to be injected into the operative end of a power handtool shown in phantom lines and in axial alignment with the container; and FIG. 2 is a view similar to FIG. 1 but showing the container in its operative position, that is, when pressed axially against the end of the dental tool holder.

DESCRIPTION OF THE PREFERRED EMBODIMENT

The collar-shaped outlet end 1 of the container 2 filled with a suitable cleaning or lubricating liquid product in the form of an aerosol associated with a suitable propergol has fitted thereon a composite insert 3 adapted to connect the output valve (not shown) of container 2 to the operative end 4 of a dental handtool to be lubricated or cleaned. In the example illustrated, this composite insert 3 is rigid with the outlet tube of the container but a detachable insert adapted to be fitted to the outlet tube of any other container may also be contemplated without departing from the basic principle of the invention.

This composite insert 3 actually comprises three elements, namely a first rigid socket 5 formed with an external end flange 6 and adapted to fit into the collar-shaped end 1 of container 2, this flange 6 bearing with its annular surface against the terminal annular surface a of said collar 1; a second socket 7 also rigid, longer than, and fitting telescopically in, the first socket 5, and provided likewise at its outer or free end with an external flange 8, its inner or fitted end being provided with an internal thicker portion 9 forming an annular shoulder b for a purpose to be explained presently; finally, a sleeve 10 of flexible, resilient material is fitted around the front portion of the second socket 7 which projects from the first socket 5, the ends of this flexible sleeve bearing against the annular shoulders of the flanges 6 and 8 of the first and second sockets.

In operation, the insert 3 is firstly fitted into the collar 1 of container 2, and the operative end 4 of the handtool is pressed axially against the container, the diameter of collar 1 being adapted to fit with a normal play into the bore 11 of the handtool. The insert 3 is pushed into the handtool 4 until a stop, consisting in this example of the outer end of a driving member 12, engages the inner annular surface b of the inner thicker portion 9 of the second socket 7.

If this axial pressure exerted against the container 2 is increased, as shown by the arrow F of FIG. 2, while so holding the handtool as to unseat the outlet valve of the container, firstly the second socket 7 will move inside the first socket 5, as a consequence of the pressure exerted by the end of driving member 12 on the inner annular shoulder b of the thicker portion 9 and also by virtue of the inherent elasticity of the flexible resilient sleeve 10 which is thus caused to undergo a deformation causing an external bead 13 to develop therein, this bead eventually forming a tight seal by engaging the inner wall of the bore 11 of the handtool, thus providing the desired fluid-tightness. Under these conditions, the lubricating or cleaning product is introduced under pressure into the body of the handtool without any risk of being forced back through the bore.

This feature is particularly advantageous when utilizing the composite insert of this invention for lubricating dental handtool holders provided with a separate internal conduit 14 for delivering a cooling fluid, this conduit opening in general into the bore 11 of the handtool holder in close vicinity of the outer end of this bore. The lengths of the second socket 7 and flexible sleeve 10 are selected to cause the bead 13 to develop beyond the port through which the inner conduit opens into the bore 11, in order to prevent any ingress of cleaning or lubricating product into the conduit.

The composite insert according to the instant invention is adaptable to various manual, power-operated tools having different inner diameters, the second socket 7 penetrating more or less deeply into the first socket 5 in order to produce a more or less pronounced distortion of the flexible sleeve 10 and thus form the sealing bead 13.

Though the insert has been described with particular reference to the injection of a lubricant contained in a pressurized container into the inner cavity of a dental handtool, it will readily occur to those conversant with the art that many other applications of this insert may be comtemplated, notably for injecting any liquid product into any desired device or member, whenever it is desired to provide a fluid-tight joint between the outlet aperture of the container and the outer end of the bore formed in said device or member.

What is claimed is:

1. A composite insert for injecting a liquid product contained in a container into a dental handpiece provided with an inner bore and an internal abutment-forming element in said bore, which comprises:

a first rigid socket formed with an external flange and adapted to fit fixedly into a collar-shaped element surrounding the outlet aperture of said container filled with said product, a second rigid socket extending forwardly from said first socket and having its rear end slidable telescopically in said first socket and provided with an annular bearing surface formed on its inner peripheral surface and adapted to engage said internal abutment-forming element of said handpiece, the front end of said second insert having an external flange, and a flexible resilient sleeve surrounding the portion of said second socket externally of said first socket, opposite ends of said sleeve bearing against said external flanges of said first and second sockets, whereby the application of an axial force to said second socket bearing surface by said abutment-forming element will cause said second socket to penetrate more deeply into said first socket and the flexible resilient sleeve to undergo an elastic deformation in the form of a bead-like swollen portion thereof projecting radially outwards for engagement with the wall of the inner bore of said handpiece in order to provide a fluid-tight joint between the outlet aperture of the container and said bore.

2. An insert according to claim 1, for use in a dental handpiece provided with an independent internal conduit port opening into said bore, wherein the length of the second socket is so selected that the bead-like swollen portion of the flexible resilient sleeve develops at a distance from the outer end of said bore which is greater than the distance between said outer end and the conduit port opening into said bore.

3. An insert according to claim 2, which constitutes an integral part of the outlet tube of a pressurized container filled with a suitable aerosol for lubricating said dental handpiece.

4. An insert according to any of claims 1 to 3, in which said abutment forming element is a driving element inside said bore of said handpiece, and in which said second socket has a bore of sufficient size to receive said driving element, and said annular bearing surface is located near the rear end of said second socket and is engageable with said driving element.

* * * * *